US009760174B1

(12) United States Patent
Letendre

(10) Patent No.: US 9,760,174 B1
(45) Date of Patent: Sep. 12, 2017

(54) HAPTIC FEEDBACK AS ACCESSIBILITY MODE IN HOME AUTOMATION SYSTEMS

(71) Applicant: EchoStar Technologies L.L.C., Englewood, CO (US)

(72) Inventor: Ellen Letendre, Englewood, CO (US)

(73) Assignee: ECHOSTAR TECHNOLOGIES INTERNATIONAL CORPORATION, Englewood, CO (US)

( * ) Notice: Subject to any disclaimer, the term of this patent is extended or adjusted under 35 U.S.C. 154(b) by 0 days.

(21) Appl. No.: 15/204,393

(22) Filed: Jul. 7, 2016

(51) Int. Cl.
G06F 3/01 (2006.01)
G08B 6/00 (2006.01)
G09B 21/00 (2006.01)
G06F 9/44 (2006.01)
A61B 5/11 (2006.01)
G07C 9/00 (2006.01)
A61B 5/00 (2006.01)

(52) U.S. Cl.
CPC ............ G06F 3/016 (2013.01); G06F 9/4443 (2013.01); G08B 6/00 (2013.01); G09B 21/003 (2013.01); G09B 21/009 (2013.01); A61B 5/0022 (2013.01); A61B 5/1112 (2013.01); G06F 3/013 (2013.01); G07C 9/00182 (2013.01)

(58) Field of Classification Search
CPC ...... G06F 3/016; G06F 9/45443; G06F 3/013; G06F 3/017; G06F 19/3418; G08B 6/00; G09B 21/003; G09B 21/009; G07C 9/00182; A61B 5/1112; A61B 5/0022; H04L 63/101; H04L 63/0272; H04L 12/66
USPC ...................................................... 340/12.54
See application file for complete search history.

(56) References Cited

U.S. PATENT DOCUMENTS

2015/0249672 A1* 9/2015 Burns ............... H04L 12/66
726/4
2017/0053469 A1* 2/2017 Cheng ............... G07C 9/00182

* cited by examiner

Primary Examiner — Ali Neyzari
(74) Attorney, Agent, or Firm — Seed IP Law Group LLP

(57) ABSTRACT

Systems and methods for providing haptic feedback in a home automation monitoring system are provided. A method for providing haptic feedback in a home automation system includes receiving an electronic command by a home automation controller, from a haptic feedback remote control device. The home automation controller determines whether the electronic command is associated with a user interface control condition stored in a haptic effects database. If so, the home automation controller accesses the haptic effects database to identify a first haptic feedback effect associated with the determined user interface control condition, and transmits a first haptic feedback command indicating the first haptic feedback effect to the haptic feedback remote control device. A haptic feedback element in the haptic feedback remote control device is then activated to provide the first haptic feedback effect to a user of the haptic feedback remote control device.

20 Claims, 4 Drawing Sheets

HAPTIC FEEDBACK AS ACCESSIBILITY MODE IN HOME AUTOMATION SYSTEMS

BACKGROUND

Technical Field

This disclosure generally relates to home automation monitoring systems and methods and, more particularly, to systems and methods for indicating a message or condition to a user of such systems through a haptic feedback remote control device.

Description of the Related Art

Home automation systems have been around for some time, and are generally well-known. Most such systems include a central controller which monitors one or more home security devices or home appliances for occurrences of one or more events, such as a motion detector being triggered, a door or window sensor being activated, or the like. A user typically communicates with the controller (e.g., to configure the system, add new devices to be monitored by the system, display messages, view a camera feed, or the like) using a remote control device programmed to communicate with and control the home automation system controller.

While conventional remote control devices may be suitable for a large portion of home automation system users, for others, such remote control devices may be confusing, difficult to use or otherwise insufficient to suitably interact with the home automation system (e.g., via a display device, such as a television or computer monitor connected to the home automation controller). Use of conventional remote control devices may be particularly challenging for persons with limited or low vision, limited or no hearing, or some combination of limited vision and hearing.

BRIEF SUMMARY

The present disclosure generally addresses the issue of notifying users in a physically detectable and meaningful way, through haptic feedback, to various conditions or events encountered in a home automation system.

Such various conditions or events may be generally classified into two groups, referred to herein as "user interface control conditions" and "home automation device status conditions." User interface control conditions refer to conditions, for which haptic feedback is provided, that are encountered while remotely controlling a home automation controller or otherwise communicating with the home automation controller via a user interface (UI) provided by the home automation controller (and displayed, for example, on a display device such as a television). For example, a user may utilize a haptic feedback remote control device to navigate a menu provided by the UI, select/deselect items, input textual information, confirm a selection or action, setup the home automation system, device management, rule configuration, adjusting or customizing settings, or the like. By providing haptic feedback from the home automation controller to a haptic feedback remote control device, based on such UI control conditions, users may more effectively navigate, control and use their home automation system through the user interface. This is particularly advantageous to users having low or limited vision and/or low or limited hearing, for whom visual indicators or audio confirmations may not be effective.

Additionally, such conditions may include status conditions related to home automation devices (i.e., home automation device status conditions) that are being monitored by the home automation controller, including for example, status conditions relating to home security devices (e.g., a door or window sensor has been activated, motion has been detected by a motion sensor, or the like), status conditions relating to home appliances (e.g., a refrigerator door is left open, the stove has been left on, a lamp has burned out, or the like), status conditions relating to home safety devices (e.g., a smoke alarm has been activated, a gas leak detector has been triggered, or the like), status conditions relating to home environmental control devices (e.g., alerting the user to a malfunctioning heating or air conditioning unit, air filter, fan, or the like) and status conditions relating to personal health and wellness devices (e.g., a heart rate sensor indicating a high or low heart rate, or the like).

The present disclosure provides systems, methods and devices that ameliorate the problems associated with conventional home automation systems and their associated remote control devices. In particular, haptic feedback may be used to provide, via a haptic feedback remote control device, indications or messages about the user's interaction with a home automation system. For example, if a user inputs a command on the haptic feedback remote control device that cannot be performed by the home automation controller, the haptic feedback device may provide haptic feedback that indicates the command cannot be performed. Additionally, the haptic feedback device may be utilized to provide haptic feedback indicating to the user that a particular event (e.g., a home security related event, such as may be detected by a motion detector, smoke alarm, security camera, or the like) has occurred. A variety of types of haptic feedback effects may be utilized by the haptic feedback device, and each type of haptic feedback effects may be associated with different conditions or messages to be conveyed to the user.

In one embodiment, a method for providing haptic feedback in a home automation system is provided. The method includes: storing, in a haptic effects database, information representing a plurality of user interface (UI) control conditions, each of the plurality of UI control conditions being associated with a respective haptic feedback effect; activating a haptic feedback accessibility mode in a home automation controller; transmitting an electronic command from a haptic feedback remote control device to the home automation controller; receiving the electronic command by the home automation controller; determining, by the home automation controller, whether the received electronic command is associated with a UI control condition stored in the haptic effects database; if the received electronic command is determined to be associated with a UI control condition stored in the haptic effects database, then: accessing, by the home automation controller, the haptic effects database to identify a first haptic feedback effect associated with the determined UI control condition; transmitting, by the home automation controller, a first haptic feedback command indicating the first haptic feedback effect to the haptic feedback remote control device; and activating a haptic feedback element within the haptic feedback remote control device, based on the first haptic feedback command, to provide the first haptic feedback effect to a user of the haptic feedback remote control device.

In another embodiment, the present disclosure provides a home automation haptic feedback system. The home automation haptic feedback system includes one or more home automation devices, a home automation controller, a haptic effects database and a haptic feedback remote control device. The home automation controller configured to monitor a status of the home automation devices and operable to provide a user interface (UI) for remotely controlling the home automation controller. The haptic effects database stores information representing a plurality of UI control conditions, with each of the plurality of UI control conditions being associated with a respective haptic feedback effect. The haptic feedback remote control device is operable to transmit an electronic command for remotely controlling the home automation controller via the UI, and the home automation controller is further configured to: determine whether the electronic command is associated with a UI control condition stored in the haptic effects database, and if the received electronic command is determined to be associated with a UI control condition stored in the haptic effects database, then: access the haptic effects database to identify a first haptic feedback effect associated with the determined UI control condition; and transmit a first haptic feedback command indicating the first haptic feedback effect to the haptic feedback remote control device. The haptic feedback remote control device is further configured to receive the first haptic feedback command and activate a haptic feedback element within the haptic feedback remote control device, based on the first haptic feedback command, to provide the first haptic feedback effect to a user of the haptic feedback remote control device.

In another embodiment, a home automation haptic feedback system is provided that includes a home security device, a home appliance and a home automation controller communicatively coupled to the home security device and the home appliance. The home automation controller is configured to: monitor a status of the home security device; monitor a status of the home appliance; determine whether the status of the home security device or the home appliance is associated with a haptic feedback condition; and transmit a haptic feedback command associated with the haptic feedback condition to a haptic feedback device in response to determining that the status of the home security device or the home appliance is associated with the haptic feedback condition.

BRIEF DESCRIPTION OF THE SEVERAL VIEWS OF THE DRAWINGS

In the drawings, identical reference numbers identify identical elements or elements in the same group and class. The sizes and relative positions of elements in the drawings are not necessarily drawn to scale. For example, the shapes of various elements and angles are not necessarily drawn to scale, and some of these elements are enlarged and positioned to improve drawing legibility.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. Well-known structures and methods associated with media content delivery have not been shown or described in detail to avoid unnecessarily obscuring descriptions of the preferred embodiments.

Unless the context requires otherwise, throughout the specification and claims which follow, the word "comprise" and variations thereof, such as, "comprises" and "comprising" are to be construed in an open, inclusive sense, for example, "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise.

The term "or" is generally employed in its sense including "and/or" unless the content clearly dictates otherwise.

The headings and Abstract of the Disclosure provided herein are for convenience only and do not interpret the scope or meaning of the embodiments.

Figure 1:
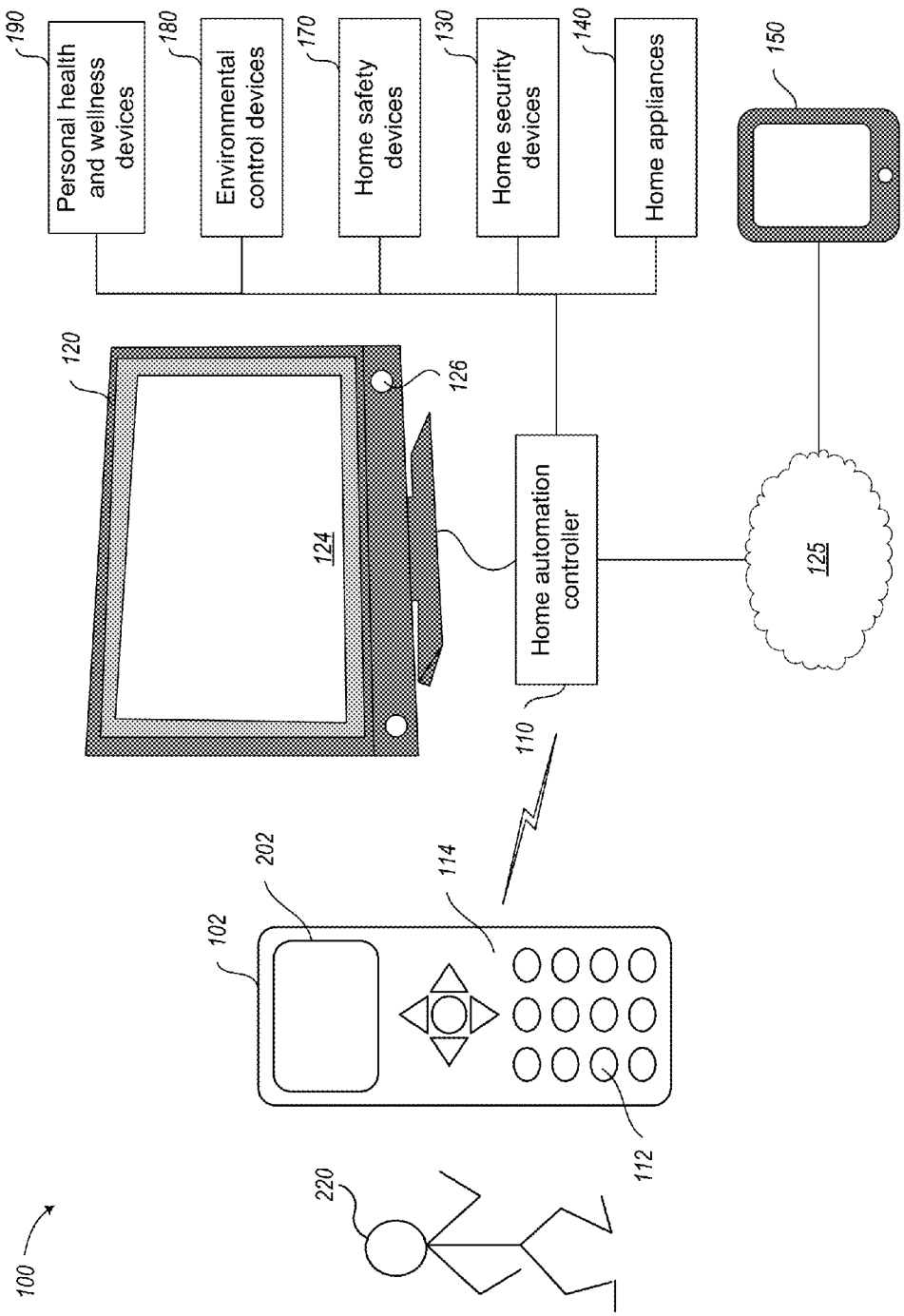
FIG. 1 is a block diagram illustrating an example home automation monitoring system including a haptic feedback device, in accordance with an embodiment of the present disclosure.

FIG. 1 is a block diagram illustrating an example home automation monitoring system 100 (which may be referred to herein as simply "system 100") including a haptic feedback device 102. It is to be appreciated that FIG. 1 illustrates just one example of a home automation monitoring system 100 and that the various embodiments discussed herein are not limited to such systems.

The home automation monitoring system 100 includes a home automation controller 110 that is communicatively coupled to one or more home security devices 130, one or more home appliances 140, one or more home safety devices 170, one or more environmental control devices 180, one or more personal health and wellness devices 190 and a display device 120.

The home security devices 130 may include any devices used for home security capable of electronic communication with the home automation controller 110, including for example, security cameras in or around a home, door or window sensors for detecting a break-in, audio alarm systems or devices, home security monitoring and communication equipment, motion detectors, motion detection lighting systems, and the like.

The home appliances 140 may include any electronically-controlled home appliances or systems, including, for example, lighting systems, televisions, audio systems, dishwashers, refrigerators, stoves, water heaters, and the like.

The home safety devices 170 may include any devices generally used for detecting and/or notifying a user of an actual or potential safety-related condition in a home. For example, the home safety devices 170 may include smoke detectors or alarms, gas detectors, and the like.

The home environmental control devices 180 may include any home environmental control systems or devices, such as heating systems, air conditioning systems, humidifiers, air filtration systems, fans, and the like.

The personal health and wellness devices may include any devices generally used for personal health and wellness and capable of electronic communication with the home automation controller 110, including for example, activity-tracking and sleep monitoring devices, smart scales, wearable devices and fobs including one or more accelerometers (e.g., for detecting falls, for counting stairs climbed, counting steps taken, etc.), smart thermometers, heart rate sensors, blood oxygen sensors, and the like.

The home automation controller 110 is a computer device that manages and controls the implementation of the home automation system 100. In particular, home automation system parameters are stored in, or otherwise accessible by, the home automation controller 110. Such parameters may be user-configurable parameters, which may be configured by accessing the home automation controller 110, for example, using the haptic feedback device 102, which in one or more embodiments may be a haptic feedback remote control device for remotely communicating with and controlling the home automation controller 110. The home automation controller 110 monitors the operational status of the home security devices 130, the home appliances 140, the home safety devices 170, the home environmental control devices 180 and the personal health and wellness devices 190 (referred to herein collectively as "home automation devices"), and may take some action (e.g., output an alarm, provide a message to a user, a security monitoring service and/or to police, or the like) based on the system parameters.

The home automation system 100 may further include one or more secondary display devices 150, which may be, for example, a mobile device such as a smartphone, a laptop computer, a tablet computer or the like. The secondary display devices 150 may be communicatively coupled to the home automation controller 110 via one or more communication networks 125. The one or more communication networks 125 may include any wired or wireless communication network or protocol, including, for example, Bluetooth, ZigBee, Z-Wave, Wi-Fi or the like.

In one or more embodiments, the home automation controller 110 may be included as part of a receiving device, such as a set-top box, cable receiver or the like that receives programming content (e.g., from audio, video, and/or data service providers, such as, but not limited to, television service providers) and provides the content to the display device 120 for viewing by one or more users 220. Accordingly, the home automation controller 110 may be any suitable converter device or electronic equipment that is operable to receive programming. Additionally, the home automation controller 110 may be an application, including any combination of software and/or hardware, that is stored on one or more servers, is accessible by the user (e.g., over one or more communication networks, such as the internet) and that is configured to control and monitor operation of the home security devices 130, the home appliances 140, the home safety devices 170, the home environmental devices 180 and the personal health and wellness devices 190.

Examples of a display device 120 include, but are not limited to, a television ("TV"), a personal computer ("PC"), a mobile device, or the like. The display device 120 includes a display 124, one or more speakers 126, and/or other output devices to communicate video and/or audio content to a user. In some implementations, one or more display devices 120 may reside in or near a customer's premises and may be communicatively coupled, directly or indirectly, to the home automation controller 110. Indirect communicative coupling may be accomplished through any wireless communication network or protocol, including, for example, Bluetooth, ZigBee, Z-Wave, Wi-Fi or the like.

Interface between the home automation controller 110 and a user 220 may be provided by the haptic feedback device 102, which in the illustrated embodiment of FIG. 1 is a haptic feedback remote control device. The haptic feedback device 102 may thus communicate with and/or remotely control the home automation controller 110 using any suitable wireless medium, such as infrared ("IR"), RF, or the like. Other devices (not shown) may also be communicatively coupled to the home automation controller 110 so as to provide user instructions. Non-limiting examples include game device controllers, keyboards, pointing devices, and the like.

It will be readily appreciated that the haptic feedback device 102 may be or include many possible physical forms and/or features, including for example, a dongle worn on a lanyard for providing haptic feedback effects, or any other wearable device through which haptic feedback can be felt by a user, in addition to a handheld remote control device. In one or more embodiments, the haptic feedback device 102 may be a haptic feedback remote control device, and a secondary haptic feedback device may be, for example, a wearable device for providing haptic feedback effects.

In the illustrated example, the haptic feedback device 102 includes an optional display 202 and a user interface 114 including a plurality of user input elements, such as buttons 112. The user interface 114 is configured to receive user input for transmitting commands to the home automation controller 110. In one example, the user interface 114 includes multiple keys or buttons 112 that the user 220 may press to initiate the commands. Such buttons 112 may include numeric buttons for inputting numeric information, directional buttons (e.g., "up," "down," "left" and "right") for menu navigation and item selection, and other special-purpose buttons (e.g., "page up," "page down," "back," "forward," "input" and so on). In another example, the user interface 114 may include a touchpad, a mouse, a joystick, a free-space position-sensing system, such as a gyroscope or accelerometer, or similar positioning device to allow a user 220 to move a cursor or other indicator on a display, such as the display device 120. The buttons 112 provided on the haptic feedback device 102 may be physical keys or buttons, or may be any other user input elements, such as graphically displayed icons which may be selected utilizing a touch screen, mouse, or the like. Further, the haptic feedback device 102 may include a microphone for receiving user input in the form of voice commands.

The haptic feedback device 102 may further include various "accessibility" features for ease of use by people, for example, having low vision and/or limited or no hearing. Such accessibility features may include indents or nodules included on buttons 112 for identifying the buttons 112 by feel. Further, the haptic feedback device 102 may include a haptic feedback enable/disable element (which may be, for example, a button 112, a sliding toggle, touch tap or any other such user interface element) which puts the haptic feedback device 102 into a haptic feedback mode. That is, the haptic feedback device 102 may operate in a "normal" or non-haptic feedback mode, or alternatively, the haptic feedback device 102 may be put into a haptic feedback mode through use of a haptic feedback mode button 112. Additionally, the haptic feedback device 102 may be put into a haptic feedback mode automatically under certain conditions. For example, if the home automation controller 110 receives user input from the haptic feedback device 102 that indicates user confusion (e.g., multiple invalid commands, or the like), then the home automation controller 110 may cause the haptic feedback device 102 to automatically enter the haptic feedback mode, in which case haptic feedback may be provided to the user via the haptic feedback device 102.

Similarly, the home automation controller 110 may include a haptic feedback accessibility mode which, when activated, causes the home automation controller 110 to provide the haptic feedback capabilities and functionalities as described herein.

In operation, the home automation controller 110 may communicate with the haptic feedback device 102 (e.g., receiving input commands from the haptic feedback remote control device) through a user interface provided by the home automation controller 110 (and displayed, for example, on the display device 120). For example, a user may utilize the haptic feedback device 102 to control the home automation controller 110 via the user interface (UI) in order to navigate a menu provided by the UI, select/deselect items, input textual information, confirm a selection or action, setup the home automation system, device management, rule configuration, adjusting or customizing settings, or the like. Certain conditions related to such navigation or control of the home automation controller 110 by the haptic feedback device 102 (i.e., user interface control conditions) may be associated with haptic feedback effects to be provided to the user by the haptic feedback device 102, as will be described in further detail herein. By providing haptic feedback from the home automation controller to a haptic feedback remote control device, based on such UI control conditions, users may more effectively navigate, control and use their home automation system through the user interface.

Further, in operation the home automation controller 110 monitors the status of all of the connected home automation devices and provides haptic feedback commands to the haptic feedback device 102 in accordance with system parameters that may associate particular home automation device status conditions (i.e., a status condition of the home security devices 130, home appliances 140, home safety devices 170, home environmental control devices 180 and personal health and wellness devices 190) with a haptic feedback effect to be provided. Such system parameters may be configurable by the user 220. For example, the user 220 may access a "settings," "rules" or similar feature in the home automation controller 110, and configure the home automation controller 110 to initiate a haptic feedback command in response to any monitored home automation device status condition as may be specified by the user 220.

Additionally, the home automation controller 110 may provide a message to the secondary display device 150 based on the monitored status conditions of the connected home security devices 130, home appliances 140, home safety devices 170, home environmental control devices 180 and personal health and wellness devices 190. This message may include a push notification and may further include a haptic effect command, which may cause the secondary display device 150 to activate a haptic element (e.g., a vibrational element in a smart phone or tablet computer) to provide haptic feedback to a user.

Figure 2:
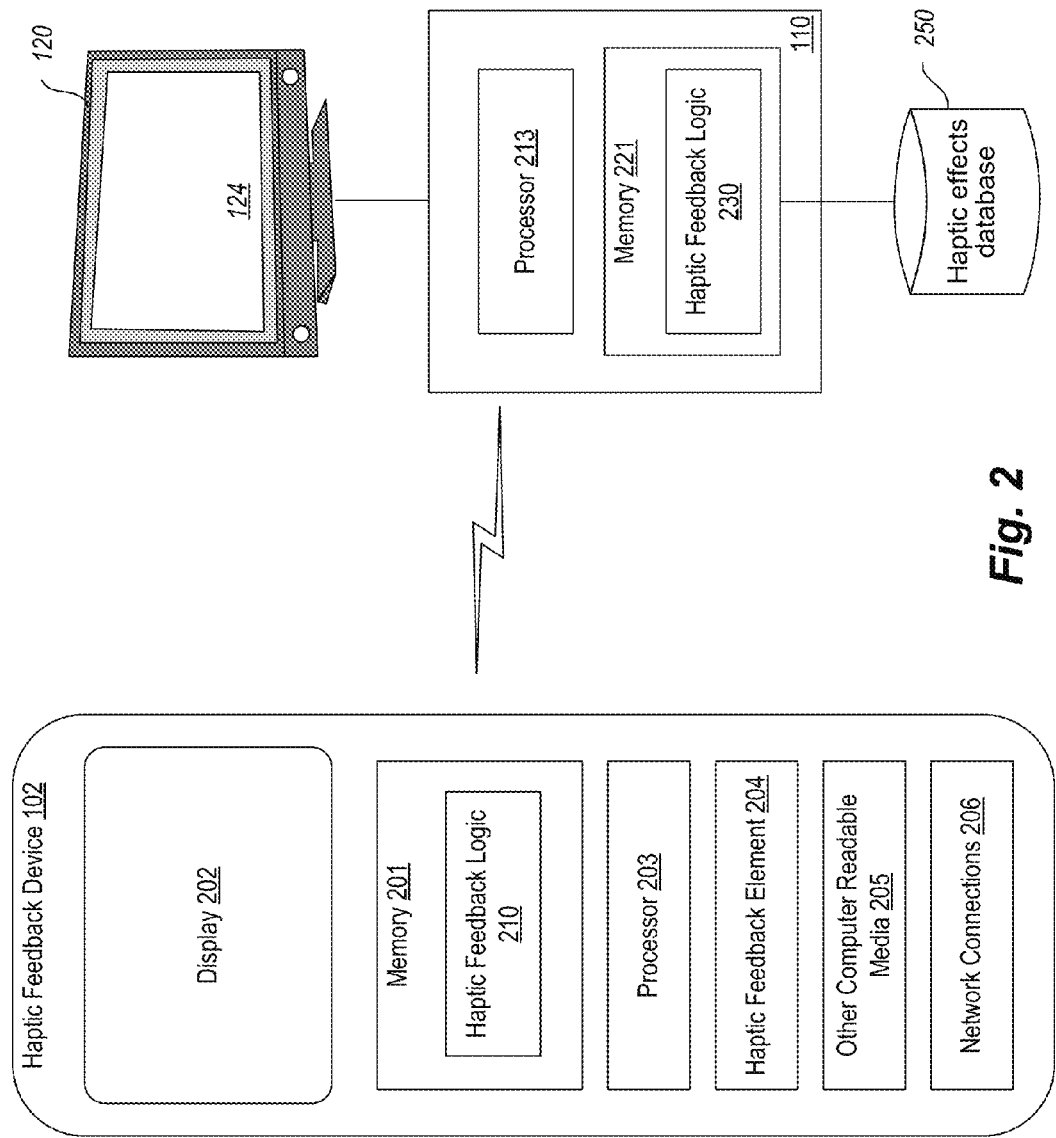
FIG. 2 is a block diagram illustrating further details of the haptic feedback device and the home automation controller, in accordance with one or more embodiments.

FIG. 2 is a block diagram illustrating further details of the haptic feedback device 102 and the home automation controller 110, in accordance with one or more embodiments. It should be noted that the components of the illustrated haptic feedback device 102 and the home automation controller 110 may be implemented in software, hardware, firmware, or in some combination to achieve the capabilities described herein.

In the embodiment shown, the haptic feedback device 102 includes a computer-readable memory ("memory") 201, one or more processors 203 and one or more haptic feedback elements 204. The haptic feedback device 102 may further include other computer-readable media 205 (e.g., flash memory, SIM card), network connections 206 and a display 202. The display 202 may be, for example, a bit-mapped LCD display having sufficient resolution to display multiple lines of text and/or other user interface elements. The network connections 206 may include one or more communication interfaces to various media devices, including but not limited to radio frequency transceivers, infrared transceivers, Bluetooth (BT), ZigBee, Z-Wave, wireless Ethernet ("Wi-Fi") interfaces, and the like.

The haptic feedback device 102 communicates with the home automation controller 110, and may further communicate with the display device 120, either directly or indirectly, for example, through the home automation controller 110 and/or a connected receiving device, such as a set-top box.

Haptic feedback logic 210 may reside in memory 201. In other embodiments, some of or all of the components of the logic 210 may be stored on and/or transmitted over the other computer-readable media 205. The logic 210 preferably executes on one or more processors 203 and manages the provision of haptic feedback by the haptic feedback device 102, as described herein. Other code or programs and potentially other data/information (not shown), may also reside in the memory 201, and preferably execute on one or more processors 203. Of note, one or more of the components in FIG. 2 may not be present in any specific implementation. For example, some embodiments may not provide other computer readable media 205.

Further, the haptic feedback logic 210 may be absent from the haptic feedback device 102, with haptic feedback management being handled instead through haptic feedback logic 230 provided in the home automation controller 110. In such a case, the determination of whether to provide haptic feedback may be made by the haptic feedback logic 230 of the home automation controller 110, which in turn may send a command to the haptic feedback device 102 to provide haptic feedback (i.e., through the haptic feedback element 204) to the user 220.

The haptic feedback logic 210 performs the haptic feedback functions of the haptic feedback device 102, as described in further detail below. In particular, the haptic feedback logic 210 determines whether haptic feedback should be provided to a user 220 of the haptic feedback device 102, and the particular haptic feedback effect to be provided (e.g., quantity, strength or intensity, duration, speed, rhythm of haptic feedback). The haptic feedback logic 210 is accessible by the processor 203, and the processor 203, upon determining a haptic feedback effect to be provided to the user 220, controls the haptic feedback element 204 to provide the determined haptic feedback effect.

In one or more embodiments, the haptic feedback logic 230 stored in the memory 221 of the home automation controller 110 may perform the haptic feedback functions described herein. For example, based on user inputs (e.g., button pushes or electronic commands issued by such button pushes) provided to the home automation controller 110 from the haptic feedback device 102, the home automation controller 110 may determine (e.g., by the processor 213 in communication with the haptic feedback logic 230) that the received user input indicates a user interface control condition (e.g., the received command cannot be performed, the user has reached a navigation edge of the UI, a response or confirmation is required, etc.) for which haptic feedback is to be provided. Additionally, the home automation controller 110 may determine, based on the monitored status of the home automation devices, whether a haptic feedback is to be provided. If a haptic feedback is to be provided, in response to a determined UI control condition or a home automation device status condition, the home automation controller 110 may access the haptic feedback effect database 250 and determine the particular type of haptic feedback effect to be provided in response to the particular condition.

The different types of haptic feedback effects which may be provided through the haptic feedback device 102 may be stored, for example, in the haptic feedback effects database 250. As such, when a condition associated with a haptic feedback effect has been detected (e.g., by the home automation controller 110), a particular type of haptic feedback effect associated with that condition may be determined by referencing the haptic feedback effects database 250.

The home automation controller 110 may thus transmit a haptic feedback command signal to the haptic feedback device 102, instructing the haptic feedback device 102 to provide the determined haptic feedback effect (e.g., via the haptic feedback element 204) to the user 220.

In some embodiments, some or all of the components/portions of the haptic feedback logic 210, 230 may be implemented or provided in other manners, such as at least partially in firmware and/or hardware, including, but not limited to one or more application-specific integrated circuits ("ASICs"), standard integrated circuits, controllers (e.g., by executing appropriate instructions, and including microcontrollers and/or embedded controllers), field-programmable gate arrays ("FPGAs"), complex programmable logic devices ("CPLDs"), and the like. Some or all of the system components and/or data structures may also be stored as contents (e.g., as executable or other machine-readable software instructions or structured data) on a computer-readable medium (e.g., as a hard disk; a memory; a computer network or cellular wireless network or other data transmission medium; or a portable media article to be read by an appropriate drive or via an appropriate connection, such as a DVD or flash memory device) so as to enable or configure the computer-readable medium and/or one or more associated computing systems or devices to execute or otherwise use or provide the contents to perform at least some of the described techniques. Some or all of the system components and data structures may also be stored as data signals (e.g., by being encoded as part of a carrier wave or included as part of an analog or digital propagated signal) on a variety of computer-readable transmission mediums, which are then transmitted, including across wireless-based and wired/cable-based mediums, and may take a variety of forms (e.g., as part of a single or multiplexed analog signal, or as multiple discrete digital packets or frames). Such computer program products may also take other forms in other embodiments. Accordingly, embodiments of this disclosure may be practiced with other computer system configurations.

The haptic feedback element 204 may be any device operable to provide a haptic feedback effect (such as, for example, a vibration effect) to a user 220 of the haptic feedback device 102. That is, the haptic feedback element 204 may be any device which provides forces, vibrations or motions to the haptic feedback device 102 that can be sensed by a user 220 (e.g., as tactile haptic feedback). In one embodiment, the haptic feedback element 204 includes a vibration element, which provides vibrational haptic feedback effects. The haptic feedback effects may be provided generally to the haptic feedback device 102, or may be provided specifically at particular portions of the haptic feedback device 102. For example, a plurality of haptic feedback elements 204 may be included in the haptic feedback device 102, with each of the haptic feedback elements 204 being operable to provide haptic feedback effects to a particular portion of the haptic feedback device 102 (e.g., vibrations provided to particular buttons 112; vibrations provided to particular areas (e.g., top, bottom, left, right) of the haptic feedback device 102).

The features of the haptic feedback device 102 can be combined with other accessibility features, such as textual bumps or nodules on the buttons 112, audio features for providing audible feedback to a user (e.g., an audible tone or buzz), visual feedback indicators (e.g., blinking lights) or the like.

Additionally, the secondary display device 150 may include one or more haptic feedback elements (not shown). For example, the secondary display device 150 may be a mobile device, such as a smartphone, that includes one or more vibrational elements that may be activated to provide a haptic effect. Accordingly, the secondary display device 150 may be caused to provide a haptic effect to a user upon receiving a haptic feedback command or notification from the home automation controller 110. The haptic feedback effects and types of haptic feedback to be provided via the secondary display device 150 may be configurable by the user, for example, through accessing the home automation controller 110 and adjusting or configuring settings for the system 100.

In one or more embodiments, the secondary display device 150 may be a mobile device that receives haptic feedback commands in response to the home automation controller 110 determining that a status of one or more of the home automation devices is associated with a home automation device status condition (i.e., a condition for which haptic feedback is to be provided). That is, in addition to providing a haptic feedback effect to the haptic feedback device 102 (in order to alert the user to the particular status of a home automation device, such as a home security device 130 being activated), the home automation controller 110 further may provide a haptic feedback command to the mobile device to alert the user to the home automation device status condition.

Figure 3:
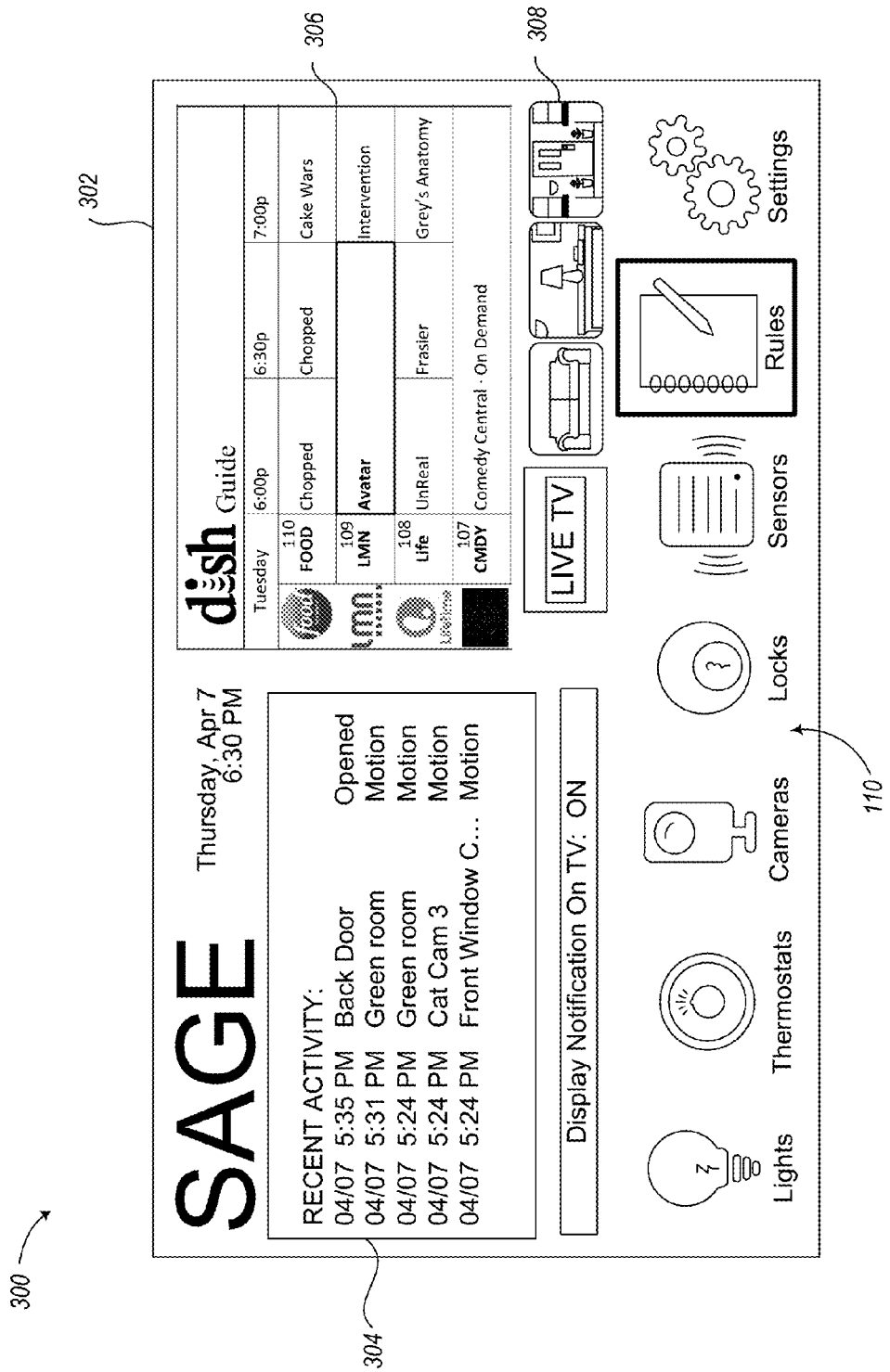
FIG. 3 illustrates an example home automation user interface which may be utilized in connection with the home automation system, in one or more embodiments.

FIG. 3 illustrates an example home automation user interface 300 which may be utilized in connection with the home automation system 100, in one or more embodiments. The home automation controller 110 may be coupled, for example, to the display device 120 or to a receiving device, such as a set-top box, that provides the user interface 300 for display on the display device 120.

As shown in FIG. 3, the user interface 300 may include a "home" display screen 302, which may be displayed as a main or default screen when accessing and viewing the home automation controller 110 via a display device 120. The home screen 302 may include a variety of features, such as a recent activity feature 304 that displays a list of one or more of the most recent home security events detected by the home automation system 100. The recent activity feature 304 may display messages indicating, for example, that the back door of the house was opened at a particular date and time, that motion was detected by a particular motion detector or camera at a particular date and time, a window was opened, and so on. The types of events or activities that are displayed in the recent activity feature 304 may be configurable by a user.

The home screen 302 provided by the user interface 300 may further include a program display window 306 that displays programming provided, for example, through a receiving device such as a set-top box or the like. Further, the home screen 302 may include one or more camera feeds 308 that display live feeds from security cameras within or outside of the house. One or more selectable icons 310 are included in the home screen 302, which when selected may provide additional screens allowing the user to view, modify or otherwise configure various home security and automation features. The selectable icons 310 may include, for example, selectable icons for lights, thermostats, cameras, locks, sensors, rules and settings, as shown in FIG. 3. It will be readily appreciated that a variety of additional selectable icons may be included, depending on the particular home security and automation features that are installed at a home.

In one or more embodiments, a user may interact with the user interface 300 using the haptic feedback device 102. For example, the haptic feedback device 102 may be a haptic feedback remote control device for controlling the home automation controller 110, in which case the user can utilize the haptic feedback device 102 to navigate through and select any of the various features, such as the recent activity feature 304, the program display window 306, the camera feeds 308, the selectable icons 310, and the like using the haptic feedback device 102. It should be readily appreciated that the user interface 300 may include a variety of menus, sub-menus, pop-up message windows or boxes, or the like, and further may at times display messages to a user which may require some interaction or input on the part of the user (e.g., "Are you sure you want to deactivate the window sensors? Please select 'Yes' or 'No'").

In one or more embodiments, the user interface 300 may include a help or tutorial feature, which may include video and audio (e.g., provided via the display device 120) explaining how to use the haptic feedback, what different types of haptic feedback indicate, and so on. The haptic feedback help or tutorial feature may be launched by navigating to a help menu via the user interface 300, or alternatively, the help or tutorial feature may be automatically launched, and displayed on the display device 120, if the home automation controller 110 detects that the user is having trouble using the haptic feedback device 102 (e.g., multiple invalid inputs, or the like). Additionally, the haptic feedback help or tutorial feature may be launched via a 'haptic feedback help' user input element, such as a button 112.

Haptic feedback effects may be provided by the haptic feedback device 102 to indicate a variety of user interface control conditions. For example, in some embodiments, haptic feedback effects may be provided to indicate that the user has navigated to or reached a limiting edge of the home automation user interface 300 (e.g., top, bottom, and side edges of the user interface 300) and that further commands received from the haptic feedback device 102 (e.g., by pressing "up," "down," "left" or "right" on the haptic feedback device 102) cannot be performed by the home automation controller 110.

In some embodiments, haptic feedback effects may be provided to indicate selection and/or deselection of highlighted items provided by the user interface 300 and displayed on the display device 120 (e.g., a check box, a "next" or "confirm" button, etc.). For example, the user interface 300 may, at times, provide various messages to a user 220 that require user input. Radio buttons and/or check box features may be provided in such messages, and the user 220 may utilize the haptic feedback device 102 to make a desired selection (such as, for example, indicating whether certain settings should be enabled or disabled) using the radio buttons and/or check box features.

In some embodiments, haptic feedback effects may be provided to a user when navigation steps such as "cancel," "back," "next," or "continue" are taken to retreat to a previous or home screen provided via the user interface 300, or to move to a next screen or step provided via the user interface 300.

In some embodiments, haptic feedback effects may be provided to distinguish, to the user 220, when a request for textual input (e.g., via user input into a text field, such as may be required for setting a custom name for a household device to be monitored by the system 100) is needed, as opposed to input via a check box selection (e.g., as may be required to set notification or haptic feedback preferences). The haptic feedback effects may be utilized to distinguish such requests for different type of inputs by, for example, providing a particular type of haptic feedback (e.g., a particular quantity of vibrational pulses, strength or intensity of vibration, speed of vibration and/or rhythm of vibrations) associated with each of the different types of input that may be requested.

Similarly, in some embodiments, haptic feedback effects may be provided to indicate, or distinguish between, state changes of the haptic feedback device 102 (e.g., enabling/disabling the haptic feedback effects or haptic feedback mode in the haptic feedback device 102, indicating entry of a sleep mode, indicating that a software update is occurring, etc.).

In some embodiments, haptic feedback effects may be provided to indicate confirmation of a user's selection (e.g., confirm a selection of "cancel" or "back") and/or to confirm that the selected actions have been taken or completed (e.g., to confirm that a selection has been canceled, or to confirm that the user interface 300 has navigated "back" to a previous screen).

In some embodiments, haptic feedback effects may be provided to indicate that a dialog or pop-up message provided by the user interface 300 needs a response. For example, a message may be provided through the user interface 300 requesting user input in the form of a selection from among "yes," "no" or "cancel" options. In such a case, haptic feedback effects may be provided to indicate that a selection is required, and further may be provided to indicate a current highlighted choice from among the options (e.g., a single vibration pulse indicating "yes" is highlighted; two vibration pulses indicating "no" is highlighted; three vibration pulses indicating "cancel" is highlighted). Additionally, haptic feedback effects may be provided to confirm that a selection from among the options has been made.

Additionally, haptic feedback effects may be provided to indicate status conditions related to any of the home automation devices (i.e., home security devices 130, home appliances 140, home safety devices 170, home environmental control devices 180 and personal health and wellness devices 190) that are being monitored by the home automation controller.

Haptic feedback effects, and particular types of haptic feedback effects, may be provided to the user (via the haptic feedback device 102 and/or the secondary display device 150) based upon a variety of user-configurable system parameters. For example, a user may access a "rules" or "settings" screen provided by the home automation controller 110, and may turn on or off haptic feedback, and further may specify a type of haptic feedback effect (e.g., by specifying the quantity, intensity, duration, speed and/or rhythm of vibrational pulses) to be provided when a particular event or condition is determined by the home automation controller 110. For example, the user may configure the system 100 to provide an intense haptic feedback effect (e.g., strong vibration effect) via the haptic feedback device 102 when the home automation controller 110 detects that a home automation device status condition is present, such as a smoke alarm has been activated, or that a window sensor has been triggered, or the like. Similarly, the user may configure the home automation controller 110 to provide a push notification to the secondary display device 150 and/or to provide a haptic feedback command to the secondary display device 150 such that the secondary display device 150 will activate a haptic feedback element (e.g., a vibrational element within a smartphone).

It should be readily understood that haptic feedback effects may be provided to indicate numerous and varied possible conditions to a user 220 of the haptic feedback device 102. For example, haptic feedback effects may be provided to indicate acknowledgement, by the home automation controller 110, of any command issued from the haptic feedback device 102. That is, every press of a button 112 on the haptic feedback device 102, once received and registered as a button-press by the home automation controller 110, may cause one or more haptic feedback effects to be provided, thus indicating to the user 220 that the button-press has been received by the home automation controller 110. Further, the home automation controller 110 may include numerous and varied functions (e.g., home security functions, home appliance functions, settings, help functions, etc.), each of which may be associated with one or more haptic feedback effects to be provided to a user 220 of the haptic feedback device 102.

The haptic feedback effects provided through the haptic feedback device 102 may be thought of as a form of communication, or language, which may be used to guide or otherwise help users of the home automation controller 110. As such, various forms of haptic feedback may be utilized to indicate a variety of conditions to users.

A wide variety of types or styles of haptic feedback effects (e.g., the types or styles of vibration effects) may be utilized by the haptic feedback device 102, in order to effectively communicate to the user a variety of conditions or messages, as described above. For example, a quantity of vibrational pulses may be utilized to communicate a message or condition to a user (e.g., one quick pulse means X, two quick pulses mean Y, three quick pulses mean Z, etc.).

Various strengths or intensities of vibration may be utilized to indicate various conditions or to communicate a message to a user. For example, a weak pulse may be provided as haptic feedback to indicate confirmation by the home automation controller 110 of a received, valid command from the haptic feedback device 102 (e.g., confirming the user has selected a particular button or choice). Similarly, a strong pulse may be provided to indicate to a user that the home automation controller 110 received an invalid command from the haptic feedback device 102 (e.g., a user input that cannot be performed by the home automation controller 110, an error or illogical selection, etc.), or to alert the user to a serious event, such as detection of a smoke or fire alarm being activated.

Various speeds of vibration may be utilized to indicate various conditions or messages. The haptic feedback device 102 may provide haptic feedback having different speeds of vibration to indicate a range of severity of detected conditions. For example, a slow, steady vibration pulse may be provided to indicate a non-emergency home automation device status condition, such as a lamp being burned out, or being left on in an unoccupied room. A fast vibration pulse may be provided to indicate a more serious condition, such as an important message being received from a critical household device such as a gas sensor.

The haptic feedback rhythm may further be varied to indicate various conditions or messages. For example, three steady vibrational pulses in a row may indicate a first condition or message, whereas two quick vibrational pulses followed by a delayed third pulse may indicate a different condition or message. Each of the various haptic feedback parameters (i.e., quantity, intensity, duration, speed and rhythm) may be combined in various ways to provide for a wide range of communication possibilities through the haptic feedback device 102. In some embodiments, the haptic feedback device 102 may be configurable, such that users may set their own preferred types of haptic feedback effects for various conditions or messages, each of which may be configured by accessing the home automation controller 110 and setting system monitoring and notification parameters as may be desired.

Haptic feedback may further be provided as a timed repeat of a previously-sent haptic effect message. For example, user interaction may be required to confirm receipt of the haptic effect, and thus acknowledge the underlying condition that triggered the haptic feedback, in order for that haptic effect to no longer be provided. If the user has not disabled or otherwise confirmed or acknowledged the message being conveyed via the haptic feedback effect, then that haptic feedback effect may be provided again as a timed repeat until the user takes some action (e.g., confirming or acknowledging the message).

The different types of haptic feedback effects which may be provided through the haptic feedback device 102 may be stored, for example, in a haptic feedback effects database (not shown) accessible by the haptic feedback logic 210 in the haptic feedback remote 100 and/or in the haptic effects database 250 accessible by the haptic feedback logic 230 of the home automation controller 110. As such, when a condition associated with a haptic feedback effect has been detected (e.g., by the home automation controller 110), a particular type of haptic feedback effect associated with that condition may be determined by referencing the haptic feedback effects database 250. Accordingly, that particular type of haptic feedback effect may be provided by the haptic feedback element 204. When a user adjusts or otherwise configures the types of haptic feedback effects to be provided in response to any detected condition by the home automation controller 110, that haptic feedback effect and associated condition may be updated and stored in the haptic effects database 250, such that the home automation controller 110 can provide the user-preferred haptic feedback effects.

Similarly, haptic feedback effects to be provided via the secondary device 150 may be configured by the user via the home automation controller 110, with the user configured preferences being stored in the haptic effects database 250, such that the user-configured haptic effects may be provided by the secondary device in response to a command or instruction from the home automation controller 110 to provide such haptic effects.

Haptic feedback effects may thus be provided to communicate a variety of UI control conditions and home automation device status conditions associated with the home automation monitoring system 100. For example, haptic feedback effects may be provided to guide the user 220 through setting up and communicating with the home automation controller 110 (e.g., for setting rules, configuring system parameters, navigating via the user interface, etc.), as well as to notify or alert the user to the status of a monitored home automation device, such as the occurrence of a particular event (e.g., a window sensor was triggered, or some similar home security or safety issue has occurred). Moreover, the haptic feedback effects may be provided by a haptic feedback device that may be an enhanced remote control device for controlling the home automation controller 110, as well as a receiving device such as a set-top box that interfaces with the home automation controller 110.

Figure 4:
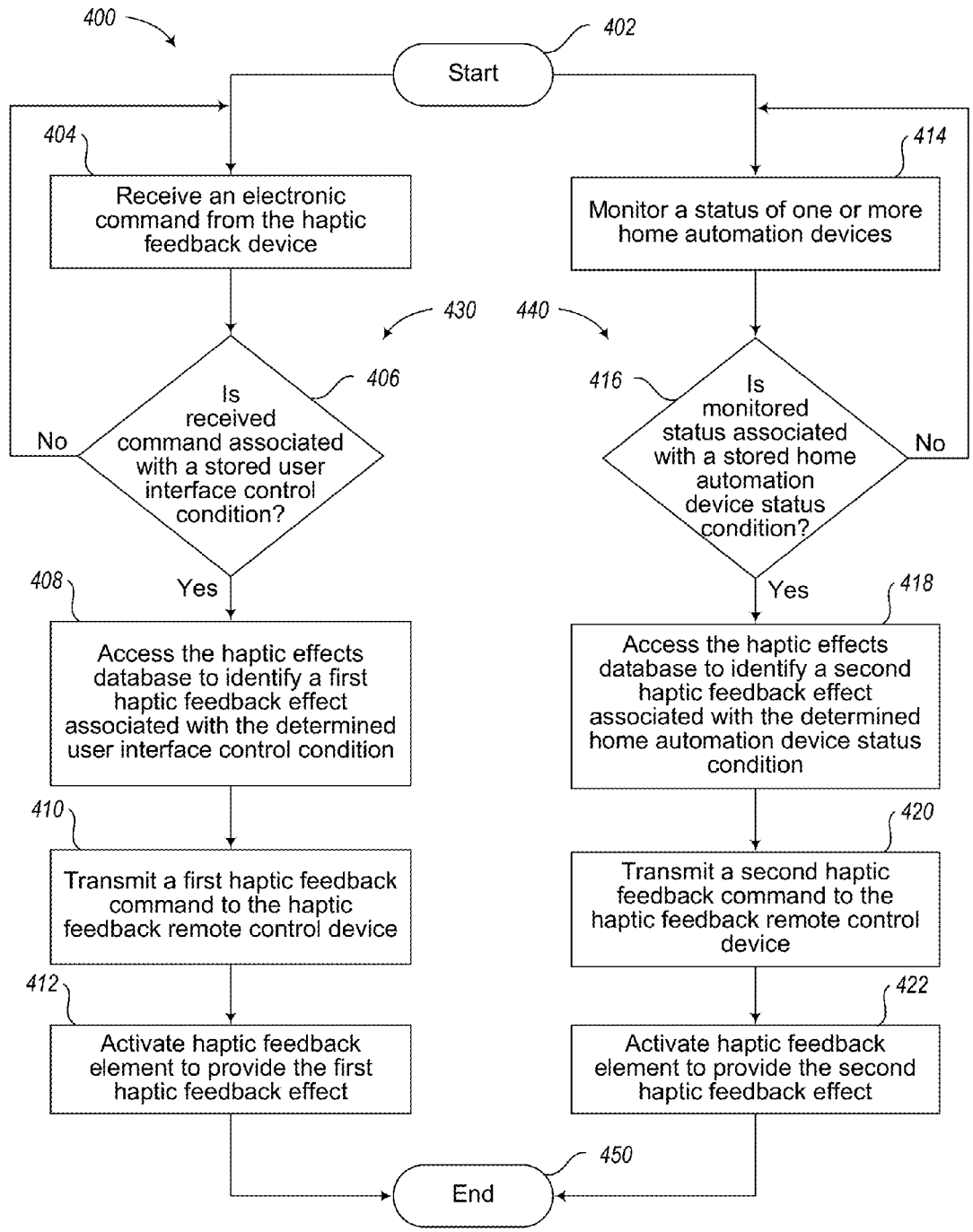
FIG. 4 is a flowchart illustrating a method for providing haptic feedback in a home automation system, in accordance with one or more embodiments.

FIG. 4 is a flowchart 400 illustrating a method for providing haptic feedback in a home automation system, in accordance with one or more embodiments.

At block 402, the method commences. In one or more embodiments, the method may commence upon activating a haptic feedback accessibility mode in the home automation controller 110 (not shown). The method then proceeds simultaneously along two branches, a user interface control condition branch 430 and a home automation device status condition branch 440.

In the user interface control condition branch 430, at block 404, the home automation controller 110 receives an electronic command issued from the haptic feedback device 102. The electronic command may be, for example, an input provided via the haptic feedback remote control device, for example, to navigate the user interface 300, to enter textual information, to select or deselect a menu item, or the like.

At block 406, the home automation controller 110 determines whether the received electronic command is associated with a user interface control condition (i.e., a user interface condition for which haptic feedback is to be provided) stored in the haptic effects database 250. If the received command is not associated with a user interface control condition, then the flow returns to the start of the method at block 402. On the other hand, if the received electronic command is determined to be associated with a UI control condition, then the flow continues to block 408.

At block 408, the home automation controller 110 accesses the haptic effects database 250 to identify a first haptic feedback effect associated with the determined UI control condition. Depending on the determined UI control condition (e.g., the user has reached a navigation edge of the UI, the received user input is invalid, the UI requires a response to a prompt or message, etc.), one of a variety of types of haptic feedback effects may be associated with the condition (e.g., effects having various quantity, intensity, duration, speed and/or rhythm characteristics). The home automation controller 110 may determine the type of haptic feedback effect associated with the particular UI control condition, for example, by referencing the haptic effects database 250, which may be configured by the user as described herein.

At block 410, the home automation controller 110 transmits a first haptic feedback command indicating the first haptic feedback effect to the haptic feedback device 102.

At block 412, the haptic feedback device 102 activates the haptic feedback element 204, based on the first haptic feedback command, to provide the first haptic feedback effect to a user of the haptic feedback device 102.

At the same time that the method for providing haptic feedback proceeds along the user interface control condition branch 430, the method also proceeds along the home automation device status condition branch 440.

In the home automation device status condition branch 440, at block 414, the home automation controller 110 monitors the status of one or more home automation devices (e.g., home security devices 130, home appliances 140, home safety devices 170, home environmental control devices 180 and personal health and wellness devices 190). The home automation controller 110 communicates with the home automation devices over any wired or wireless communication network in order to monitor the status of the devices. The monitored status may include monitoring the status of the connected devices in view of the system rules, settings or parameters that may be set up or configured within the home automation controller 110.

At block 416, the home automation controller 110 determines whether the status of a monitored home automation device is associated with a home automation device status condition (i.e., a home automation device status condition for which haptic feedback is to be provided) stored in the haptic effects database 250. This determination may be made by the home automation controller 110, for example, by accessing the haptic feedback logic 230 and/or the haptic effects database 250, which may include logic and/or database associations for determining whether and to what extent (e.g., what type) haptic feedback should be provided in response to particular statuses of the home security device 140. If the monitored status is not associated with a home automation device status condition, then the flow returns to the start of the method at block 402. On the other hand, if the monitored status is determined to be associated with a stored home automation device status condition, then the flow continues to block 418.

At block 418, the home automation controller 110 accesses the haptic effects database 250 to identify a second haptic feedback effect associated with the determined home automation device status condition. As discussed herein, a variety of types of haptic feedback effects may be provided to indicate a variety of conditions or messages. Depending on the determined home automation status condition (e.g., a window sensor has been activated, a smoke or gas detecting device has been activated, a lamp is inoperable, etc.), one of a variety of types of haptic feedback effects may be associated with the status condition (e.g., effects having various quantity, intensity, duration, speed and/or rhythm characteristics). The home automation controller 110 may determine the type of haptic feedback effect associated with the particular home automation status condition by referencing the haptic effects database 250, which may be configured by the user as described herein.

At block 420, a second haptic feedback command indicating the second haptic feedback effect is transmitted from the home automation controller 110 to the haptic feedback device 102. The second haptic feedback command may include, for example, a particular type of haptic feedback effect that should be provided on the haptic feedback device 102.

At block 422, the haptic feedback device 102 activates the haptic feedback element 204, based on the second haptic feedback command, thereby providing the second haptic feedback effect to the user.

At block 414, the method ends; however, the home automation controller 110 may continue to receive electronic commands from the haptic feedback device 102 and monitor the status of the home automation devices, and thus may proceed along either branches 430, 440 of the method at any point in time in which a received electronic command and/or a monitored status of the home automation devices is associated with a haptic feedback condition.

The above description of illustrated embodiments, including what is described in the Abstract, is not intended to be exhaustive or to limit the embodiments to the precise forms disclosed. Although specific embodiments and examples are described herein for illustrative purposes, various equivalent modifications can be made without departing from the spirit and scope of the disclosure, as will be recognized by those skilled in the relevant art.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for providing haptic feedback in a home automation system, comprising:
   storing, in a haptic effects database, information representing a plurality of user interface (UI) control conditions, each of the plurality of UI control conditions being associated with a respective haptic feedback effect;
   activating a haptic feedback accessibility mode in a home automation controller;
   transmitting an electronic command from a haptic feedback remote control device to the home automation controller;
   receiving the electronic command by the home automation controller;
   determining, by the home automation controller, whether the received electronic command is associated with a UI control condition stored in the haptic effects database;
   if the received electronic command is determined to be associated with a UI control condition stored in the haptic effects database, then:
      accessing, by the home automation controller, the haptic effects database to identify a first haptic feedback effect associated with the determined UI control condition;
      transmitting, by the home automation controller, a first haptic feedback command indicating the first haptic feedback effect to the haptic feedback remote control device; and
      activating a haptic feedback element within the haptic feedback remote control device, based on the first haptic feedback command, to provide the first haptic feedback effect to a user of the haptic feedback remote control device.

2. The method of claim 1, further comprising:
   storing, in the haptic effects database, information representing a plurality of home automation device status conditions, each of the plurality of home automation device status conditions being associated with a respective haptic feedback effect;
   monitoring, by the home automation controller, a status one or more home automation devices;
   determining, by the home automation controller, whether the status of a monitored home automation device is associated with a home automation device status condition stored in the haptic effects database;
   if the status of the monitored home automation device is determined to be associated with a home automation device status condition stored in the haptic effects database, then:
      accessing, by the home automation controller, the haptic effects database to identify a second haptic feedback effect associated with the determined home automation device status condition;
      transmitting, by the home automation controller, a second haptic feedback command indicating the second haptic feedback effect to the haptic feedback remote control device; and
   activating the haptic feedback element within the haptic feedback remote control device, based on the second haptic feedback command, to provide the second haptic feedback effect to the user of the haptic feedback remote control device.

3. The method of claim 2, further comprising:
   transmitting, by the home automation controller, a mobile device haptic feedback command indicating the second haptic feedback effect to a mobile device; and
   activating a haptic feedback element within the mobile device, based on the mobile device haptic feedback command, to provide the second haptic feedback effect to a user of the mobile device.

4. The method of claim 2, wherein monitoring a status of one or more home automation devices includes monitoring at least one of: a home security device, a home appliance, a home safety device, a home environmental control device and a personal health and wellness device.

5. The method of claim 1, further comprising:
   determining, by the home automation controller, a type of haptic feedback effect to be provided to the user.

6. The method of claim 5, wherein the type of haptic feedback effect to be provided is selected from among a plurality of types of haptic feedback effects, each of the types of haptic feedback effects being distinguishable from one another based on at least one of: quantity, intensity, duration, speed and rhythm of the haptic feedback.

7. The method of claim 5, wherein determining a type of haptic feedback effect to be provided includes determining a portion of the haptic feedback remote control device to experience the haptic feedback effect.

8. The method of claim 1, wherein the haptic feedback element within the haptic feedback remote control device includes a vibration element.

9. A home automation haptic feedback system, comprising:
   one or more home automation devices;
   a home automation controller configured to monitor a status of the home automation devices and operable to provide a user interface (UI) for remotely controlling the home automation controller;
   a haptic effects database storing information representing a plurality of UI control conditions, each of the plurality of UI control conditions being associated with a respective haptic feedback effect; and
   a haptic feedback remote control device operable to transmit an electronic command for remotely controlling the home automation controller via the UI,
   wherein the home automation controller is further configured to:
      determine whether the electronic command is associated with a UI control condition stored in the haptic effects database, and if the received electronic command is determined to be associated with a UI control condition stored in the haptic effects database, then:
         access the haptic effects database to identify a first haptic feedback effect associated with the determined UI control condition; and transmit a first haptic feedback command indicating the first haptic feedback effect to the haptic feedback remote control device, and wherein the haptic feedback remote control device is further configured to receive the first haptic feedback command and activate a haptic feedback element within the haptic feedback remote control device, based on the first haptic feedback command, to provide the first haptic feedback effect to a user of the haptic feedback remote control device.

10. The home automation haptic feedback system of claim 9, wherein the haptic effects database further stores information representing a plurality of home automation device status conditions, each of the plurality of home automation device status conditions being associated with a respective haptic feedback effect, the home automation controller being further configured to:

determine whether the status of a monitored home automation device is associated with a home automation device status condition stored in the haptic effects database, and if the status of the monitored home automation device is determined to be associated with a home automation device status condition stored in the haptic effects database, then:
  access the haptic effects database to identify a second haptic feedback effect associated with the determined home automation device status condition; and
  transmit a second haptic feedback command indicating the second haptic feedback effect to the haptic feedback remote control device, and wherein the haptic feedback remote control device is further configured to receive the second haptic feedback command and activate the haptic feedback element to provide the second haptic feedback effect to the user of the haptic feedback remote control device.

11. The home automation haptic feedback system of claim 10, further comprising a mobile device having a mobile device haptic feedback element, wherein the home automation controller is further configured to transmit a mobile device haptic feedback command indicating the second haptic feedback effect to the mobile device, and the mobile device is configured to activate the mobile device haptic feedback element, based on the mobile device haptic feedback command, to provide the second haptic feedback effect to a user of the mobile device.

12. The home automation haptic feedback system of claim 11, wherein the mobile device comprises a wearable haptic feedback device.

13. The home automation haptic feedback system of claim 10, wherein the one or more home automation devices includes at least one of: a home security device, a home appliance, a home safety device, a home environmental control device and a personal health and wellness device.

14. The home automation haptic feedback system of claim 9, wherein the home automation controller is configured to determine a type of haptic feedback effect to be provided to the user, wherein the type of haptic feedback effect to be provided is selected from among a plurality of types of haptic feedback effects, each of the types of haptic feedback effects being distinguishable from one another based on at least one of: quantity, intensity, duration, speed and rhythm of haptic feedback.

15. The home automation haptic feedback system of claim 14, wherein the home automation controller is further configured to determine a portion of the haptic feedback remote control device to experience the haptic feedback effect.

16. The home automation haptic feedback system of claim 9, wherein the haptic feedback element within the haptic feedback remote control device includes a vibration element.

17. The home automation haptic feedback system of claim 9, wherein the haptic feedback remote control device includes a haptic feedback mode enable/disable input element, the haptic feedback mode enable/disable input element being operable to selectively enter the haptic feedback remote control device into a haptic feedback mode, wherein in the haptic feedback mode the haptic feedback remote control device is operable to provide haptic feedback effects.

18. A home automation haptic feedback system, comprising:
  a home security device;
  a home appliance;
  a personal health device;
  a home automation controller communicatively coupled to the home security device, the home appliance and the personal health device, the home automation controller being configured to:
    monitor a status of the home security device;
    monitor a status of the home appliance;
    monitor a status of the personal health device;
    determine whether the status of the home security device, the home appliance or the personal health device is associated with a haptic feedback condition; and
    transmit a haptic feedback command associated with the haptic feedback condition to a haptic feedback device in response to determining that the status of the home security device, the home appliance or the personal health device is associated with the haptic feedback condition.

19. The home automation haptic feedback system of claim 18, wherein the haptic feedback device comprises a remote control device operable to remotely control the home automation controller.

20. The home automation haptic feedback system of claim 18, wherein the haptic feedback device comprises a wearable haptic feedback device.

* * * * *